United States Patent [19]

Hu et al.

[11] Patent Number: 5,821,287

[45] Date of Patent: Oct. 13, 1998

[54] PHOTOCHROMIC PIGMENT

[75] Inventors: Andrew Teh Hu; Wen Hishin Wang, both of Hsinchu, Taiwan

[73] Assignee: National Science Council, Taipei, Taiwan

[21] Appl. No.: 695,775

[22] Filed: Aug. 8, 1996

[51] Int. Cl.$^6$ .......................... C08K 5/34; C07D 265/34; C08F 26/06
[52] U.S. Cl. ................................. 524/89; 544/99; 526/260
[58] Field of Search ................................ 544/99; 524/89; 526/260

[56] References Cited

U.S. PATENT DOCUMENTS 5,246,989  9/1993  Iwamoto et al. ........................... 524/89

Primary Examiner—Kriellion S. Morgan
Attorney, Agent, or Firm—Beveridge, DeGrandi, Weilacher & Young, L.L.P.

[57] ABSTRACT

The present invention is related to the synthesis of a novel photochromic compound. This compound is a reactive photochromic spirooxazine pigment. Its structure is shown as below:

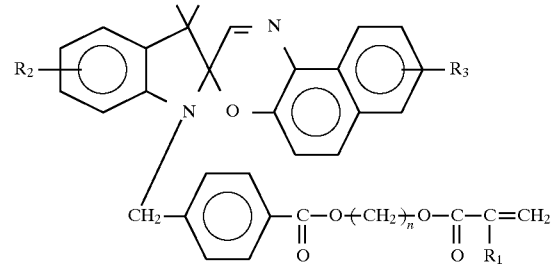

wherein $R_1$ is either a hydrogen atom or an alkyl group containing 1 to 5 carbon atoms. $R_2$ and $R_3$ are any of the following group: an alkyl group having 1 to 10 carbon atoms, or an alkyoxy group having 1 to 10 carbon atoms, or halogen atoms, or hydrogen atoms. The range of n is from 1 to 4, which represents the number of repeated units. This synthesized compound possesses a high thermal resistant property up to 241° C., and it may be added into low melting polyethylene terephthalate(PET) resins for direct melt spinning to prepare photochromic fiber. In addition, the reactive double bond of this compound can be copolymerized with other vinyl monomers, to prepare high molecular weight photochromic materials used for photochromic eye glasses and/or photochromic coating.

17 Claims, 14 Drawing Sheets

FIG.3(a)
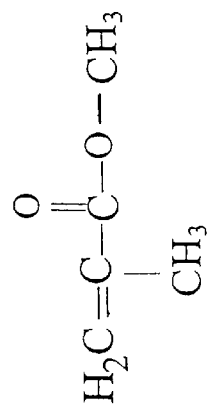
Methyl methacrylate
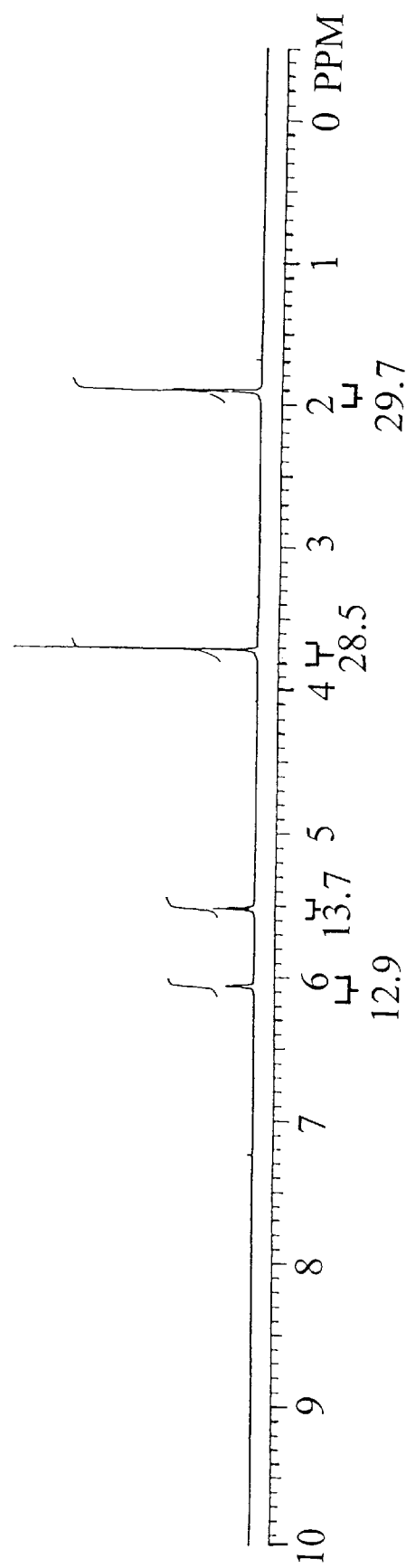

FIG. 3(b)
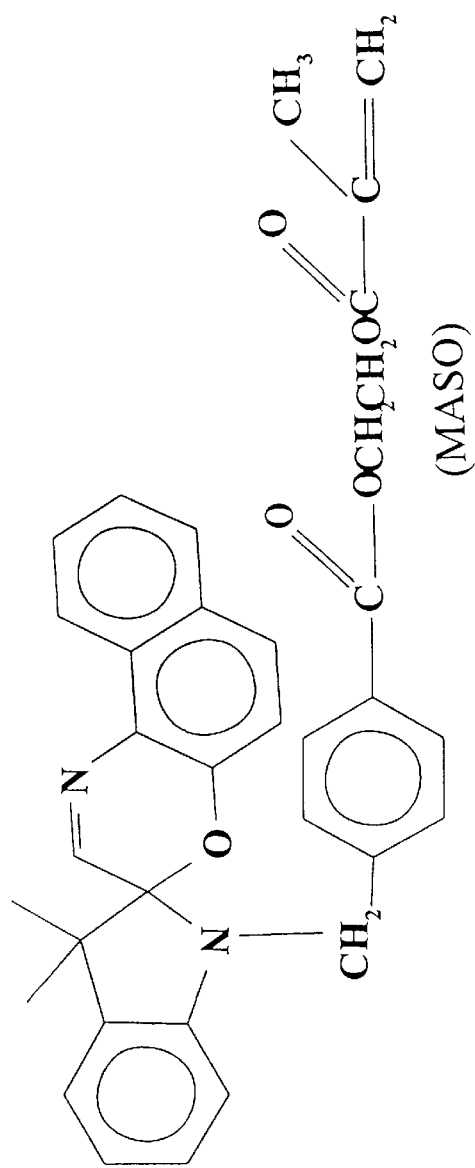
(MASO)
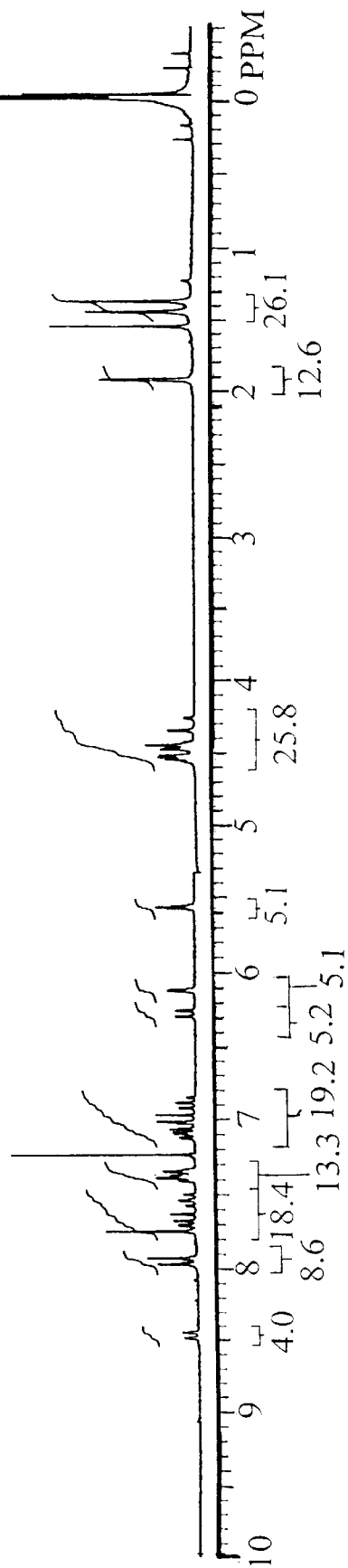

Poly(methyl methacrylate)

Poly(methyl methacrylate) contain Spirooxazine

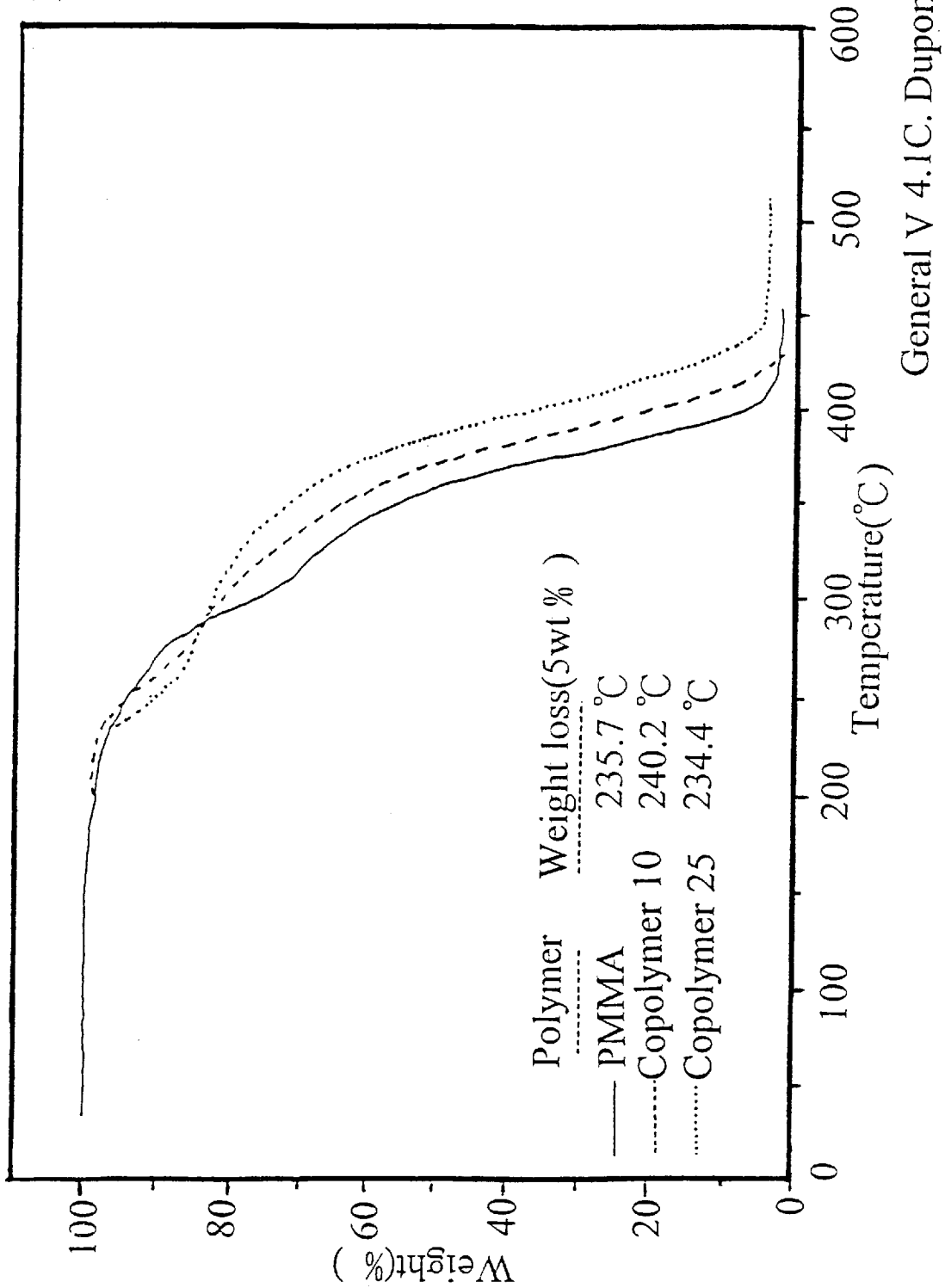

FIG. 5(a)
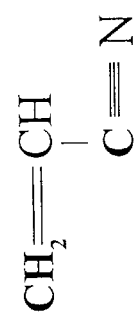
Acrylonitrile
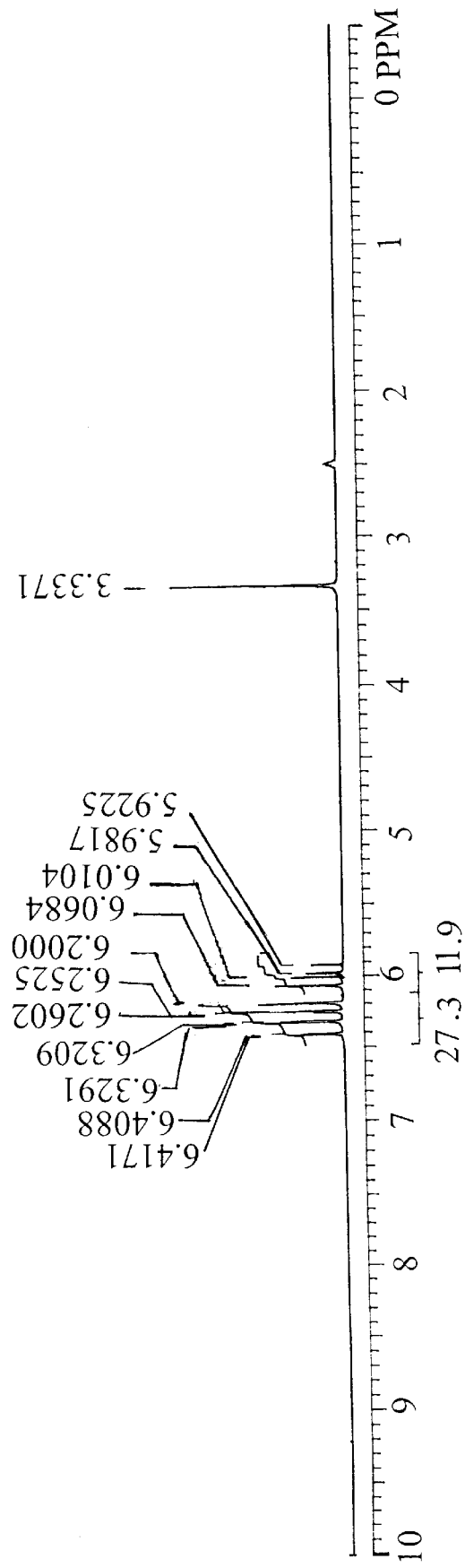

PHOTOCHROMIC PIGMENT

FIELD OF THE INVENTION

The present invention is related to the synthesis of a novel photochromic compound.

BACKGROUND OF THE INVENTION

Reactive photochromic pigment refers to pigments with structure containing not only functional group such as spirooxazine(photochromic) but also chemically reactive group such as —C=C—, —COOH, —NH$_2$, —OH etc. The latter may form chemical bonding or undergo polymerization or copolymerization with other monomeric substrates. In general, photochromic high molecular weight copolymer formed by chemical bonding has better physical properties than those formed by blending method. These materials can be used for photoelectric elements, optical memory devices, photochromic fibers, etc.

The earliest report on color change with light was in 1876 by E. ter Meer(Annalen 181, 1), on his study of dinitromethane upon light exposure. Then in 1899, W. Marckwald et al. (Z. Phys. Chem. (Leipzig) 30, 140) observed color change in dihydro-2,3,4,4-terachloronaphthalene crystal upon sunlight exposure. This material changes from colorless to purple, but colorless will be resorted when placed in the dark. Marckwald named this type of reversible color change as "Phototropy". The term "photochromism" was proposed by Y. Hirshberg (Compt.rend, 231, 903) in 1950. A material with photochromic property must be able reversible changing its visible light absorption spectrum upon irradiation of light or energy. In general, the color change by light can be expressed as follows:

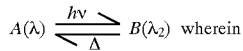

$$A(\lambda) \underset{\Delta}{\overset{h\nu}{\rightleftharpoons}} B(\lambda_2) \text{ wherein}$$

A refers to the original status of photochromic material,
B refers to the photochromic material exposed to light.

In the preparation of photochromic material, photochromic pigment is usually blended with substrate material, such as high polymers or inorganics. Heat resistance of the photochromic pigment and its compatibility with the substrate are matters of great concern, especially in the preparation of photochromic fibers. Previously the latter such as Japanese Patent S60-21975 (1985) and P1-168911(1989) are made simply by coating the fiber with photochromic dyes. Poor performance after washing can be expected. However this problem can be resolved nowadays by the adaptation of melt spinning of the photochromic pigment with high polymer substrate to enhance the quality of the photochromic fiber.

Y-R Hwa et al. (U.S. Pat. No. 5,213,733, 1993 and No. 5,422,181, 1995) proposed a method of encapsulating organic photochromic pigment in microcapsules in the melt spinning process for photochromic fiber preparation. The encapsulation serves as a barrier to protect the pigment during melt spinning. D. Jones et al. (Molec. Phys. 67, (5)1053–1064, 1989) revealed that addition of photochromic pigment to high polymer may cause aggregation, phase separation, and compatibity problems, if the concentration of the pigment was high. S. Yamamoto et al.(Japan Patent No. S61-233,079, 1986 and No. S63-275,587, 1988) reported that introducing a benzyl group to the nitrogen atom at indolenine ring of spirooxzine, it may improve the endurance of light fatigue. Y. Shlomo et al.(Liquid Crystal 8(5), 677–686, 1990) revealed that modification of spirooxazine photochromic pigment by esterification or Schiff base may enhance its thermal resistance. Combining information and concepts from these studies, the present invention has devised a means to synthesize a novel photochromic pigment with high thermal resistance suitable for melt spinning process in the photochromic fiber production.

SUMMARY OF THE INVENTION

The object of the invention is related to the synthesis of a novel photochromic compound. This compound is a reactive photochromic spirooxazine pigment.

The other object of the invention is to increase the thermal decomposition temperature (Td) of the forementioned pigment(III) to 241° C., and the pigment(III) may be added into low melting polyethylene terephthalate(PET) resins for direct melt spinning to prepare photochromic fiber.

The further object of the invention involves the reactive double bond of this pigment(III) which can be copolymerized with other vinyl monomers, to prepare high molecular weight photochromic materials used for photochromic eye glasses and/or photochromic coating.

BRIEF DESCRIPTION OF THE DRAWINGS

A. Processes
Scheme 1. Synthesis of photochromic pigment(III)
Scheme 2. Synthesis of copolymer(MMA/III)
Scheme 3. Synthesis of copolymer(AN/III)

B. Table
Table 1. Solution properties of pigment(III) and CSO
Table 2. Color change of photochromic pigments in organic solvent
Table 3. Reaction conditions for synthesis of copolymer(III)
Table 4. Analysis of pigment content in copolymers (MMA/III)
Table 5. Properties of copolymer(MMA/III)
Table 6. Reaction conditions of synthesis of copolymer (AN/III)
Table 7. Color change of photochromic fibers
Table 8. Decoloration rate of photochromic polymer film prepared by pigment(III) with PMMA
Table 9. Decoloration rate of photochromic polymer C. Figures
FIG. 1. Thermal Gravimetric Analysis (TGA) Curves of Pigment(III) and Commercial Spirooxazine(CSO).

DETAILED DESCRIPTION OF THE INVENTION

Figure 1:
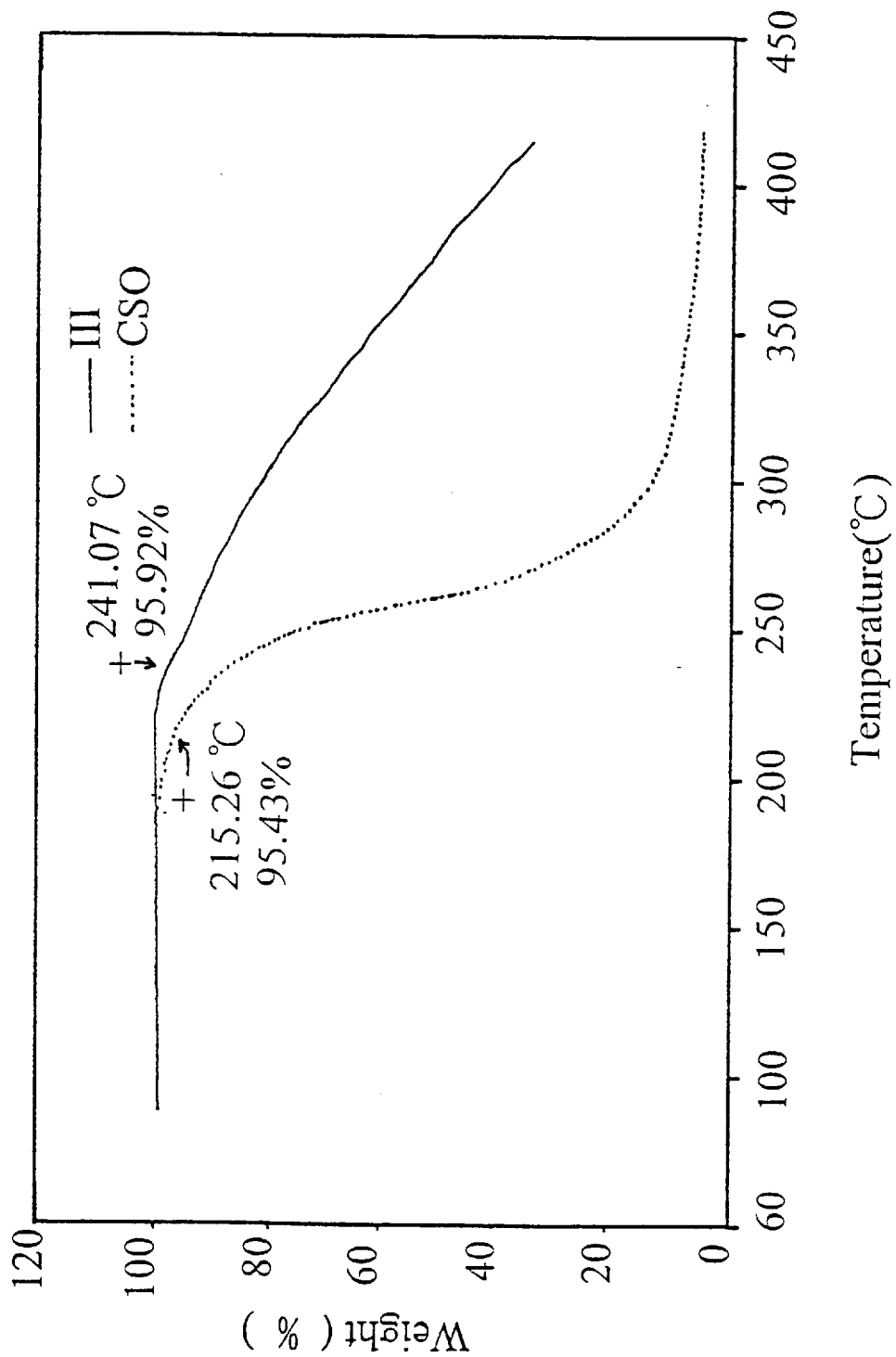

The present invention is related to the synthesis of a novel photochromic compound. This compound is a reactive photochromic spirooxazine pigment. Its general structure is shown as below:

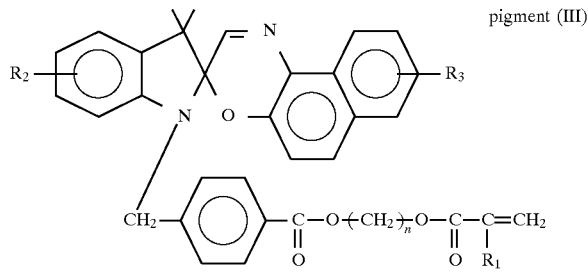

pigment (III)

wherein $R_1$ can be either a hydrogen atom or an alkyl group containing 1 to 5 carbon atoms. $R_2$ and $R_3$ represent any of the following: an alkyl group having 1 to 10 carbon atoms, an alkyoxy group having 1 to 10 carbon atoms, halogen atoms, or hydrogen atoms. The range of n is from 1 to 4, which represents the number of repeated units.

The synthesis method involves several steps that can be described as follows:

(a) Synthesis of pigment(III)—a photochromic pigment. The process was illustrated in Scheme 1 and Example 1.

Solvents used in synthesis of pigment(III) included protic and aprotic solvents, such as methanol, acetone, ethylacetate, ether, toluene, dimethylformamide. In addition, photochromic compound can be used for direct melt spinning method to prepare photochromic fiber.

The pigment(III) can further be used as a monomer for copolymerization and/or to be blended with low melting point polyester, polydimethyl isophthalate(DMI), polypropylene(PP), polymethyl methacrylate(PMMA), polyethylene terephthalate(PET) and its blends etc. for preparation of photochromic fibers.

(b) Synthesis the photochromic polymethyl methacrylate copolymers or polyacrylonitrile copolymer, were shown in Scheme 2 and Scheme 3. The preparation method wherein can be selected from one of the following preparation methods: free radical copolymerization, suspension polymerization solution polymerization, and bulk polymerization.

The present invention is illustrated by the following nonlimiting example.

EXAMPLES

Example 1

Synthesis of 1-[4'-(2"- Methacryloxy) ethoxycarbonyl][benzyl-3-3-dimethylspiro[indoline-2,3'-[3H]-naphtho[2,1-b]-1,4-oxazine(pigment III).

The process of synthesis is illustrated in Scheme 1. A detailed description of synthesis is explained as follows:

(a) Synthesis of 2-[4'-iodomethyl benzoyloxy] ethylmethacrylate(I)

9.45 g of 4-chloromethylbenzoylchloride(4-CMBC) (0.05 mole) and 6.45 g of 2-hydroxyethylmethacrylate(HEMA) (0.05 mole) were weighted and placed in double neck round flasks, followed by dissolving in benzene with stirring. Upon being completely dissolved, 3.95 g of pyridine was added dropwise at 10° C., and then the temperature was raised to 40° C. with continuously stirring for 3 hours. When reaction was completed, the reaction solution was filtered, and NaI and acetone were then added for further reaction. The reaction temperature was maintained at 40° C. for 3 hours, then residual solid was filtered and discarded by suction. The filtrate was then concentrated, and was recrystallized twice in a mixture of acetone and n-hexane. The final product was a light yellow crystal, the yield was 78% (14.6 g), the melting point of the product was between 53°–55° C.

Results of spectral analysis were shown as follows:
$^1$H-NMR(CDCl$_3$, δ, ppm):1.94(s,3H,—CH$_3$),
4.55(m, 6H, —CH$_2$),
5.6(t, 1H, —C═C—H, J=2.64 Hz),
6.13(s, 1H, —C═C—H),
7.43–7.45(d, 2H, Ar-H, J=8.36 Hz),
7.96–7.98(d, 2H, Ar-H, J=8.36 Hz)

| Element Analysis | C$_{14}$H$_{15}$O$_4$I | (374.18) | |
|---|---|---|---|
| Calculated | C44.94 | H4.04 | |
| Found | C44.71 | H4.09 | |

(b) Synthesis of 1-[4'-(2"-Methacryloxy)ethoxycarbonyl] benzyl-3,3-dimethyl-2-methylene indolenine(II)

A mixture of 3.74 g of product(I) from (a) (0.01 mole) and 1.75 g of 2,3,3-trimethyl indolenine (0.011 mole) was placed in double neck round flasks, and temperature was raised to 80° C. Upon stirring 3 hours for reaction, temperature was cooled down to room temperature. The reaction mixture was neutralized to pH 8 by adding 5% of sodium carbonated solution. The crude product was then extracted and separated by a column with an eluent comprised of EA/Hexane mixture in a ratio of 1 to 5. The final product was an oily and sticky liquid, the yield was 67%.

Results of spectral analysis were shown as follows:
$^1$H-NMR(CDCl$_3$, δ, ppm):1.38(s, 6H, —CH$_3$, gem),
1.92(s, 3H, —CH$_3$),
2.84(d, 2H, N—C═CH$_2$, J=14.56 Hz),
3.45(5, 2H, —CH$_2$, J=9.32 Hz),
4.53(t, 2H, —CH$_2$—, J=9.24 Hz),
5.56(t, 1H, —C═C—H, J=2.72 Hz),
6.11(s, 1H, —C═C—H),
6.45–7.97(m, 8H, Ar-H)

| Element Analysis | C$_{25}$H$_{27}$NO$_4$ | (405.49) | |
|---|---|---|---|
| Calculated | C74.05 | H6.71 | N3.45 |
| Found | C73.01 | H6.61 | N3.71 |

(c) Synthesis of 1-[4'-(2"-methacryloxy) ethoxycarbonylbenzyl-3,3-dimethyl-spiro [indoline-2,3'-naphtho[2.1-b]-1,4-oxazine](pigment III)

Mixture of 2.63 g product(II) (6.5 m mole) and 1.12 g of 1-Nitroso-2-naphthol (6.5 m mole) was placed in a round neck flask, 20 ml of anhydrous methanol was added, and the solution was kept stirring until solid was completely dissolved. The solution was then heated and refluxed under nitrogen for 2 hours. When reaction was completed, solvent was sucked out and the residual solid was dried under vacuum. The final product was light yellowish color, the yield was 22% (0.8 g).

Results of spectral analysis were shown as follows:
$^1$H-NMR(CDCl$_3$, δ, ppm):1.39(s, 3H),
1.46(s, 3H),
4.30–4.56(m, 6H),
5.58(s, 1H),
6.14(s, 1H),
6.29(d, 1H, J=7.72 Hz),
6.88–7.97(m, 13H),
7.76(s,1H, HC═N—),
8.48–8.50(d, 1H, J=8.36 Hz)

| Element Analysis | C$_{35}$H$_{32}$N$_2$O$_5$ | (560.65) | |
|---|---|---|---|
| Calculated | C74.98 | H5.75 | N5.00 |
| Found | C74.35 | H5.55 | N4.90 |

Example 2

Determination of the thermal resistant property of photochromic pigment(III)

The pigment(III) obtained from the Example 1 was tested for its thermal resistance. The weight loss of the sample under heat from 40° C. to 600° C. was analyzed by a Dupont thermal gravimetric analyzer model 951(TGA) under dry nitrogen, and the temperature was elevated at a rate of 10° C./min. The TGA indicated that the thermal decomposition temperature(Td) for pigment(III) with 5 wt % loss was 241° C.

Comparative Example 1

Determination of the thermal resistant property of the commercial pigment(CSO).

Figure 2:
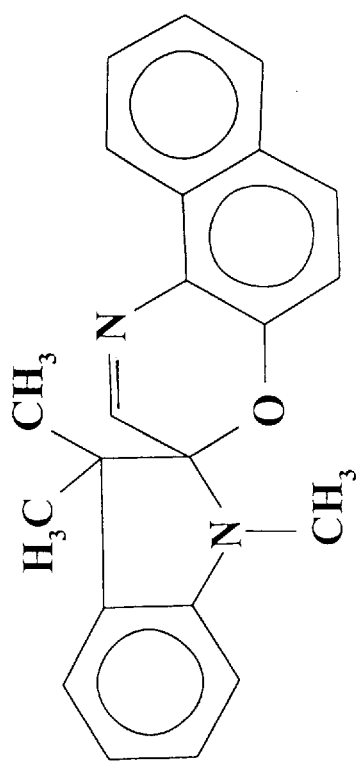
FIG. 2. Chemical Structure of commercial Spirooxazine (CSO).

The test condition of thermal resistance analysis for this example was set to be the same as previous example 2. And the test sample was a commercial pigment(CSO), its structure was shown in FIG. 2. The experimental results indicated that Td was 215° C. for CSO. Thus, the pigment(III) has higher thermal resistance than that of CSO. It leads to much better thermal resistant performance during melt spinning when the temperature is 220° C. and up, for example in the preparation of photochromic PET fibers. The CSO will be decomposed at this temperature and shows no photochromic properties.

Example 3

Solution properties of the photochromic pigment (III)

A variety of solvents were added to each portion of 0.015 g pigment(III) respectively. Solutions was kept stirring at room temperature for overnight in order to observe the status. Results were shown in Table 1.

The solubility of a commercial pigment(CSO) was tested for the purpose of comparison. Testing method and conditions were as same as Example 3. Results were listed in Table 1.

Example 4

Photochromic property of the pigment (III) in organic solvent.

A solution was prepared by dissolving the pigment(III) in chloroform to make final concentration of 50 ppm(parts per million). The solution was exposed to UV light for 10 minutes for observation. The UV light absorbency and visible light absorbency of the photochromic pigment(III) in the solvent were measured by a spectrophotometer.

Comparative Example 2

Determination of the photochromic property of the pigment(III) in organic solvent.

Method and testing conditions were the same as that in the Example 4, except the photochromic pigment(III) was substituted by the commercial pigment(CSO). Results are shown in Table 2.

Example 5

Synthesis and Identification of photochromic Polymethyl methacrylate Copolymers (a) Detailed steps for synthesis was shown in Scheme 2. Reaction conditions were listed in Table 3. Steps of synthesis were as follows: This reaction was a free radical copolymerization. At the beginning, the pigment(III) monomer (from Example 1) was mixed with methyl methacrylate monomer in several different ratios. Each mixture was placed in a reaction bottle and 0.25 wt % of AIBN (azodiisobutyronitrile) catalyst was added to solution. The solution was stirred under N$_2$ atmosphere and kept 80° C. for 10 hrs. Methanol was introduced to precipitate the polymers. Toluene was used as solvent to wash out the monomers. Purification procedure was performed several times. The final copolymers was dried under vacuum and a light yellowish solid was obtained.

(b) Structure analysis by $^1$H-NMR

Figure 3C:
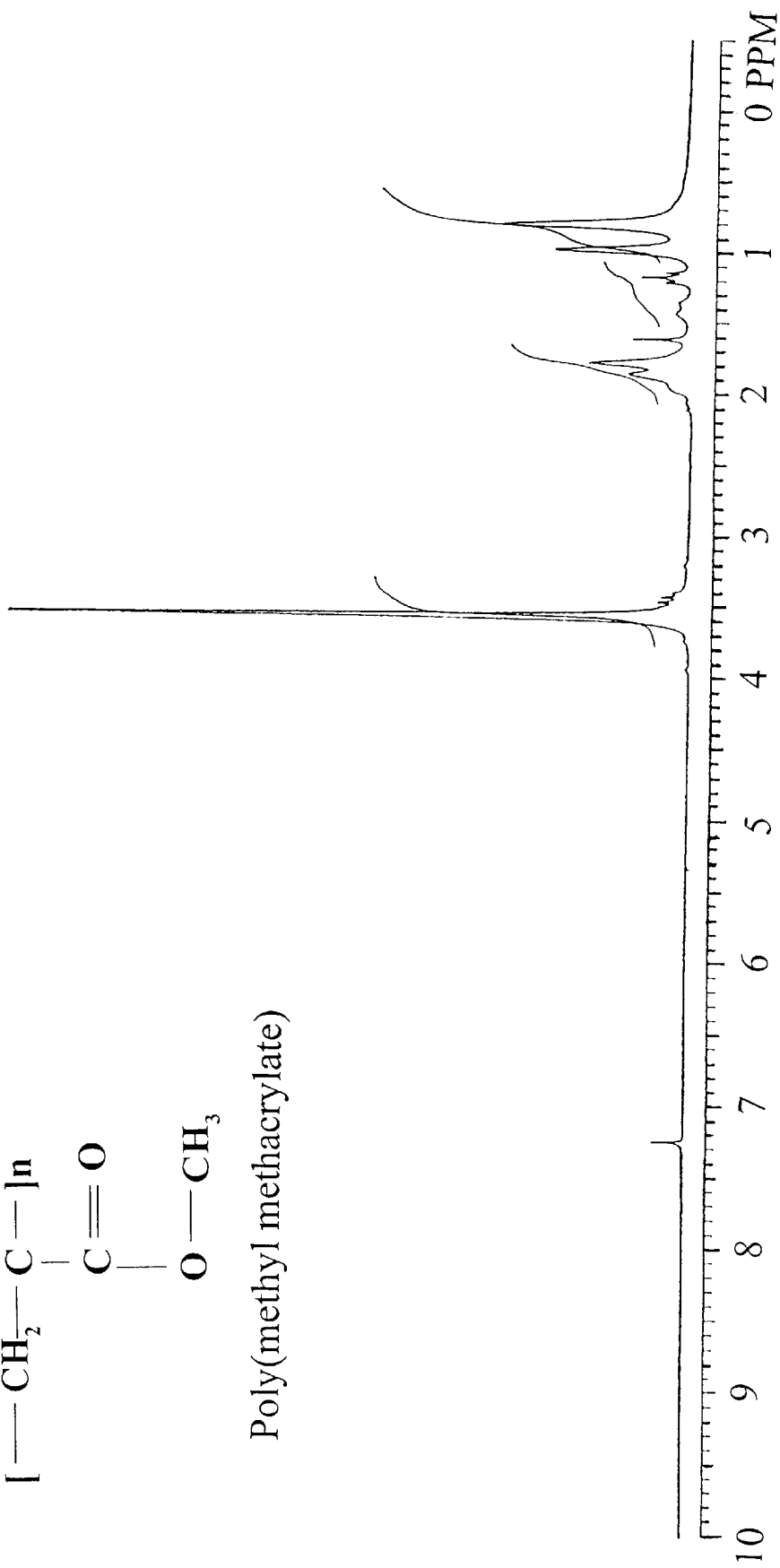
FIG. 3. $^1$H-NMR Spectrum of copolymer(MMA/III).
  a. methyl methacrylate
  b. pigment (III)
  c. poly(methyl methacrylate)
  d. copolymer(MMA/III)
FIG. 4. TGA curves of copolymers with different compositions.
Figure 3D:
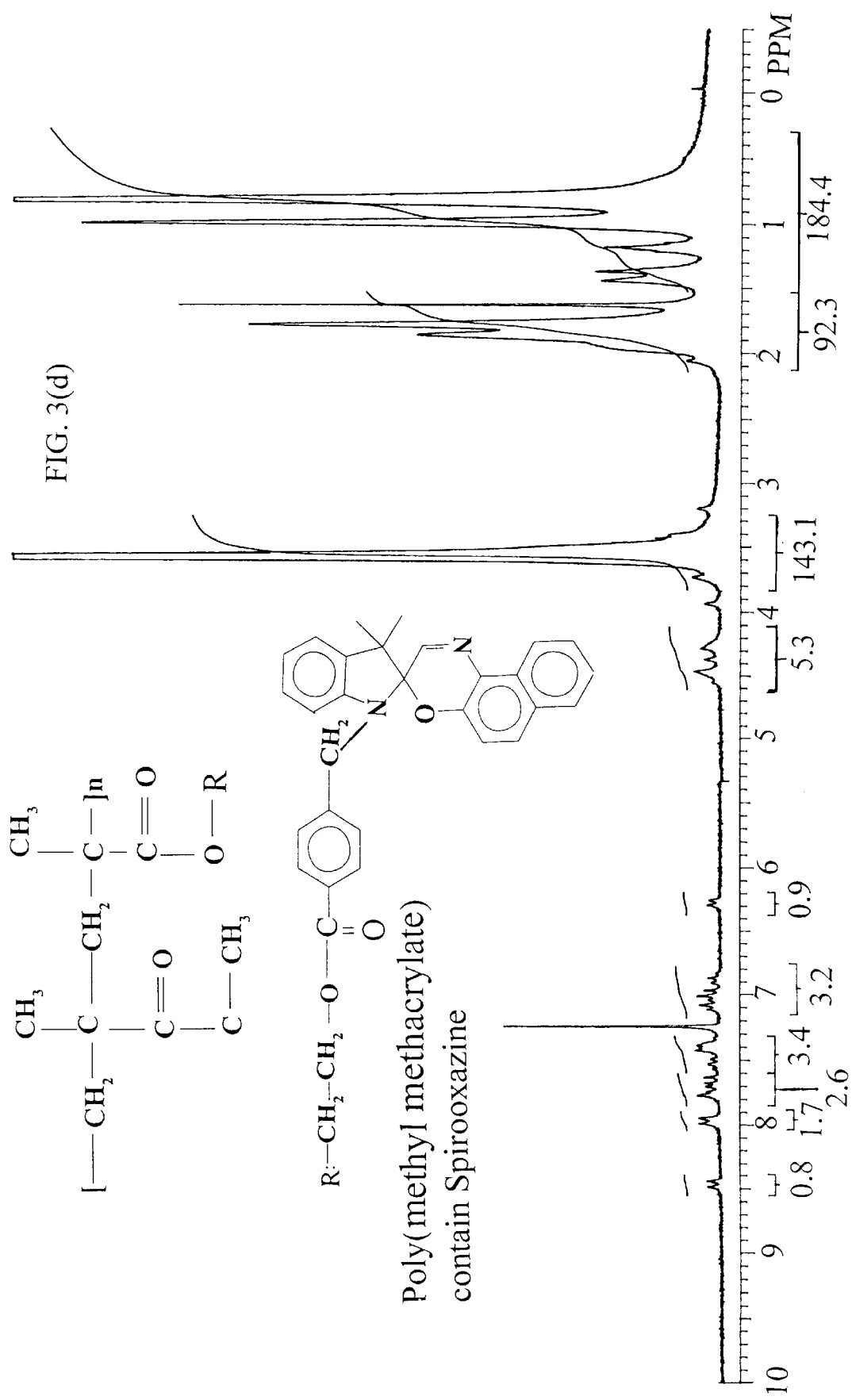

Copolymer obtained in (a) was dissolved in d-CDCl$_3$ to be analyzed by a 200 MHz NMR. Results of analysis were shown in FIG. 3. FIG. 3$a$ and 3$b$ were spectra of MMA monomers and pigment(III); 3$c$ and 3$d$ were spectra of PMMA homopolymer and photochromic copolymer, respectively. By comparison of spectra of a, b, c, and d, the disappearance of hydrogen absorption in the double bond confirms the occurrence of polymerization reaction. It also confirms the basic composition of PMMA and Spirooxazine in the final copolymer (c) Using the element analysis, the amount of pigment(III) in the copolymer can be identified via the nitrogen content. Results were shown in Table 4.

Example 6

Physical and chemical studies of photochromic spirooxazine (a) Determination of molecular weight The photochromic copolymer obtained in Example 5 was dissolved in tetrahydrofuran to make a final concentration of 1 wt % solution. This solution was passed through a chromatography column (Waters) with a RI detector to determine the molecular weight of the copolymer. The flow rate was 1 ml/minute, the calibration cure was established by using six kinds of polystyrene with different know molecular weights. Results were shown in Table 5.

(b) Measurement of glass transition temperature (Tg)

An appropriate amount of the photochromic copolymer obtained in Example 5 was taken to a Dupont DSC model 901, equipped with mechanical cooling accessory system, to determine the glass transition temperature. The temperature is calibrated against an indium standard. Samples of 3 to 5 mg were scanned at a rate of 10° C./min. Results were listed in Table 5.

(c) Measurement of thermal resistance of photochromic copolymer

Sample of copolymer obtained in Example 5 was placed in a Dupont TGA model 951 to determine the thermal resistance. Heating rate was 10° C./minute under dry nitrogen. Weight loss of sample was determined between 40° C. to 600° C. The result was shown in FIG. 4.

Example 7

Synthesis and identification of photochromic polyacrylonitrile copolymer (a) Procedure of synthesis was given in Scheme 3. Reaction conditions were listed in Table 6. Steps of synthesis were shown as follows: pigment(III) was mixed with acrylonitrile monomer in a reaction bottle, then dimethylformamide(DMF) containing 0.25 wt % AIBN was added into the bottle. The solution was degassed by $N_2$ three times. The temperature was raised to 70° C., and reaction time was 10 hours long. At the end of reaction, acetone was used as precipitating agent. The step of precipitation-washing was repeated several times. The final copolymer was collected and dried under vacuum. The appearance of the solid was light red. Under exposure to UV light, the color of the solid was blue.

(b) Structure analysis by $^1$H-NMR

Figure 5B:
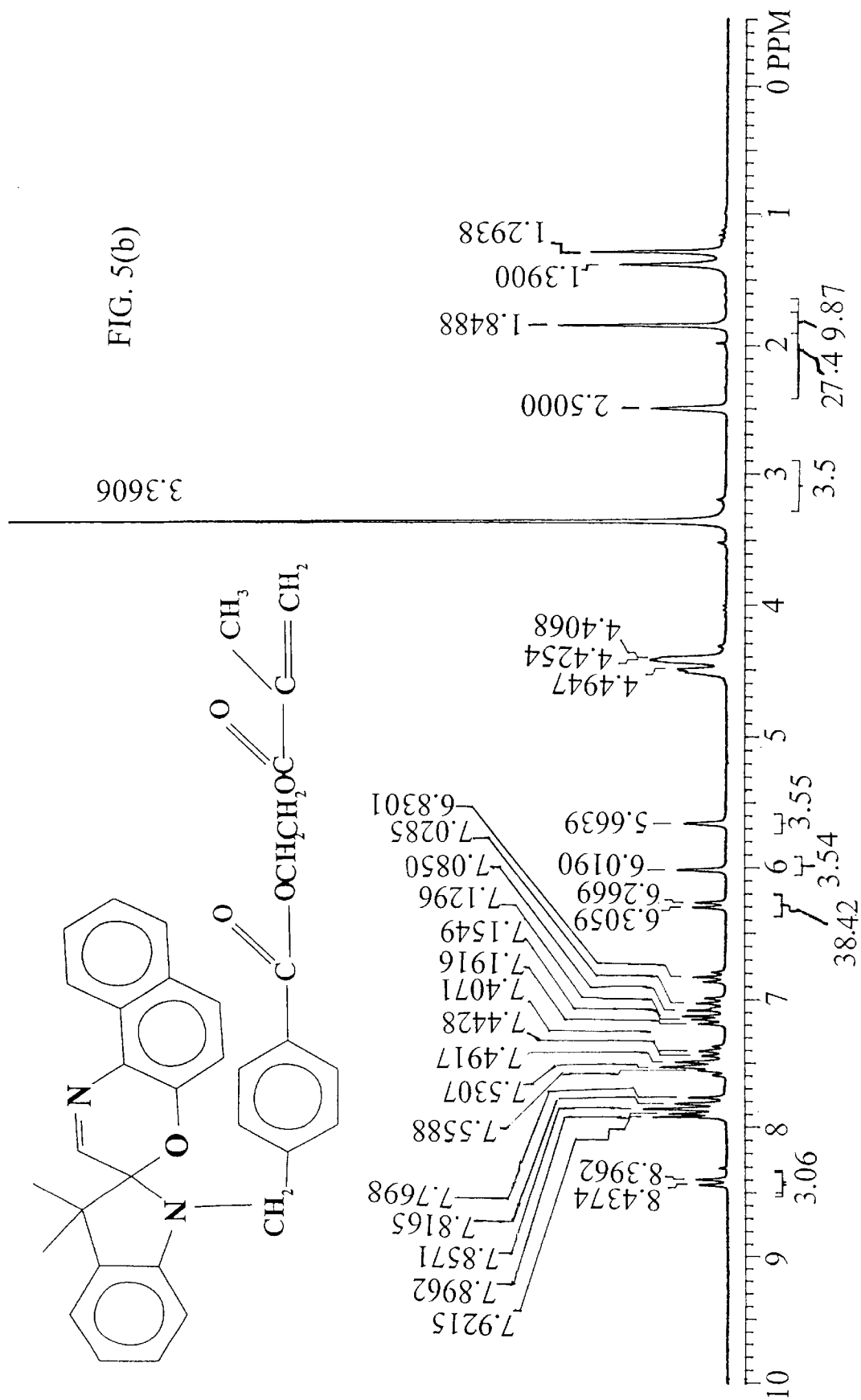
FIG. 5. $^1$H-NMR spectra of Acrylonitrile, Pigment (III) PAN and Copolymer(AN/III).
  a. Acrylonitrile,
  b. Pigment(III)
  c. Poly(Acrylonitrile)
  d. copolymer(AN/III).
Figure 5C:
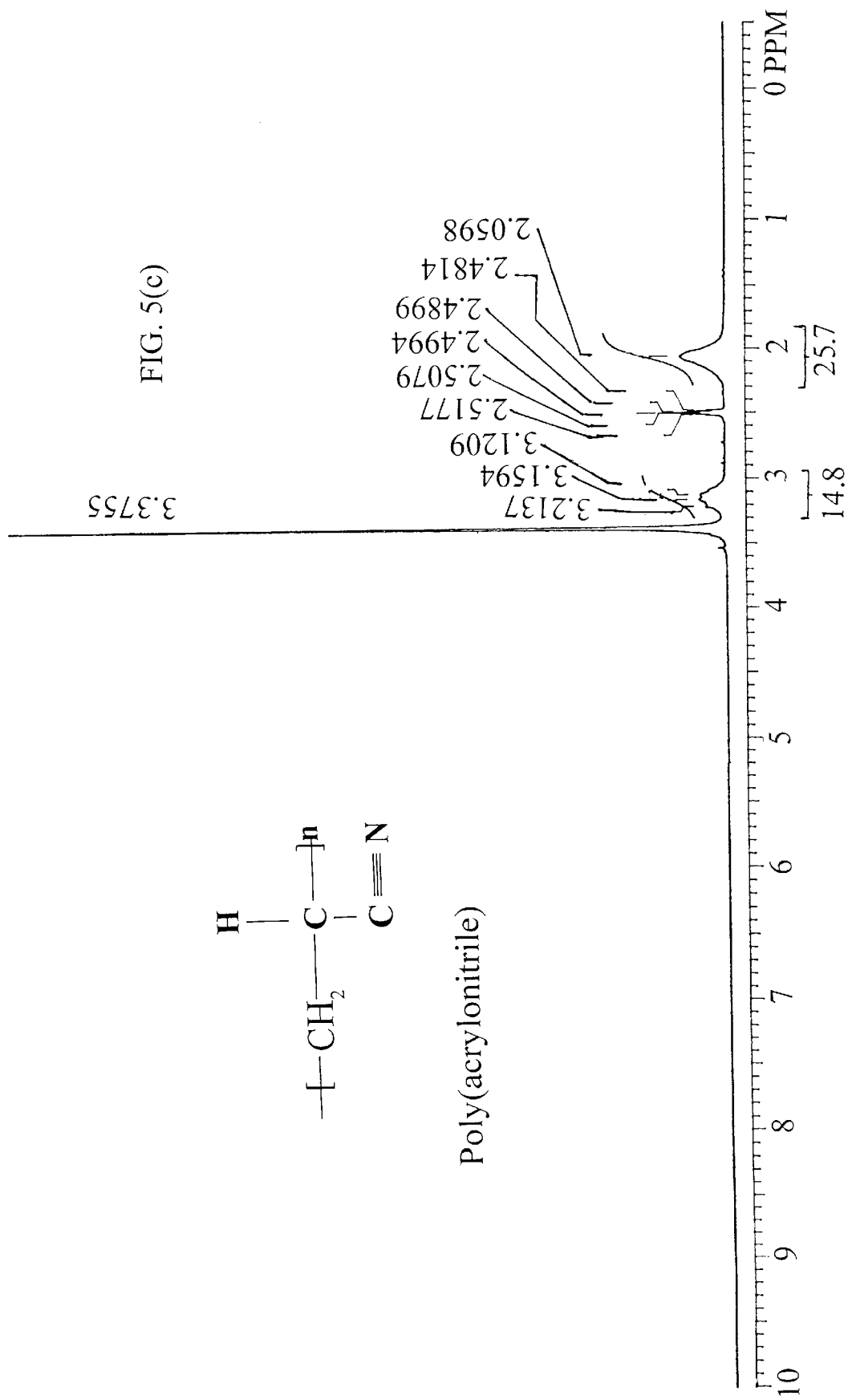
Figure 5D:
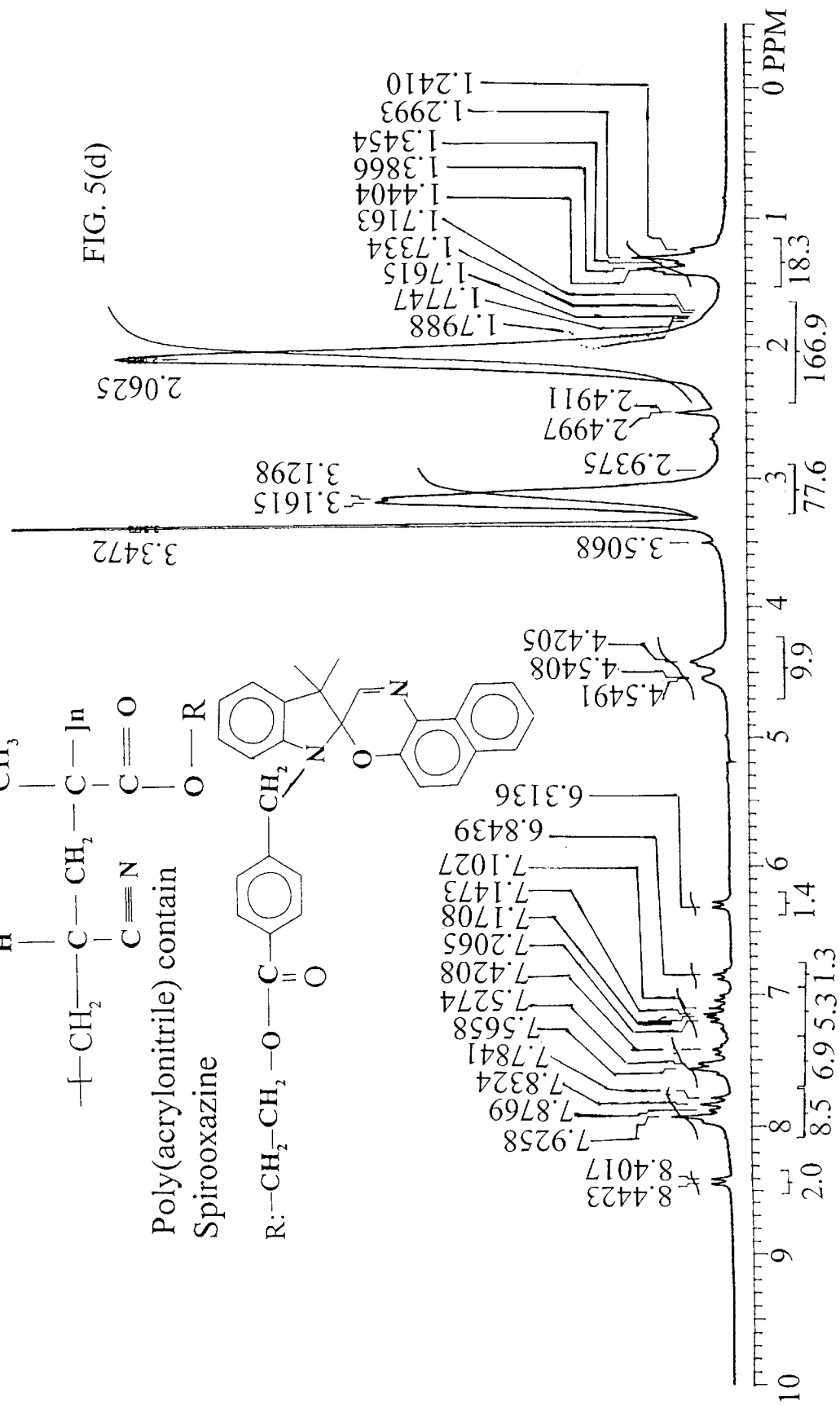

The copolymer obtained previously was dissolved in $d_6$-DMSO, and analyzed by 200 MHz NMR. The spectrum was shown in FIG. 5.

Example 8

Preparation of photochromic polypropylene fiber

To prepare photochromic polypropylene fiber, 50 mg of pigment III, was taken and dissolved in 2.0 ml of ether, followed by adding 4.95 g of polypropylene granules. After mixing well, ether was sucked out, and solution was dried to obtain uniform photochromic polypropylene granules. The fiber was made at 220° C. by a melt spinning machine made by Bradford University Inc. The photochromic fiber was then exposed under UV light (wavelength was 365 nm, power was 80 w). The result of observation was shown in Table 7.

Example 9

Preparation of photochromic polyester fiber

Low melting point PET(mp=190° C.) granules were placed in a 90° C. oven for drying five hours. Upon water removal, operation procedures in example 8 were followed to obtain photochromic polyester fiber. The result of UV exposure was listed in Table 7.

Example 10

Preparation of blending type of polymer film.

Pigment(III) was placed in a round bottle neck, and tetrahydrofuran was added to dissolve the pigment while stirring. Three solutions containing 10% of solid, with pigment content of 7.5%, 17%, and 25% were prepared respectively. These solutions were sprayed evenly by a bar coater onto a 1 mm cover glass, and dried under vacuum. At the end, a film of 10 um was obtained. Upon exposure to UV light for 20 minutes, the photochromic film changed from light yellow to blue. When measured with a UV spectrophotometers, the maximum absorbance was 570 nm. When light removed, polymer film turned back to light yellow. This step was repeated several times, and results indicated this color change was reversible.

Example 11

Preparation bonding type of photochromic polymer film.

Figure 6:
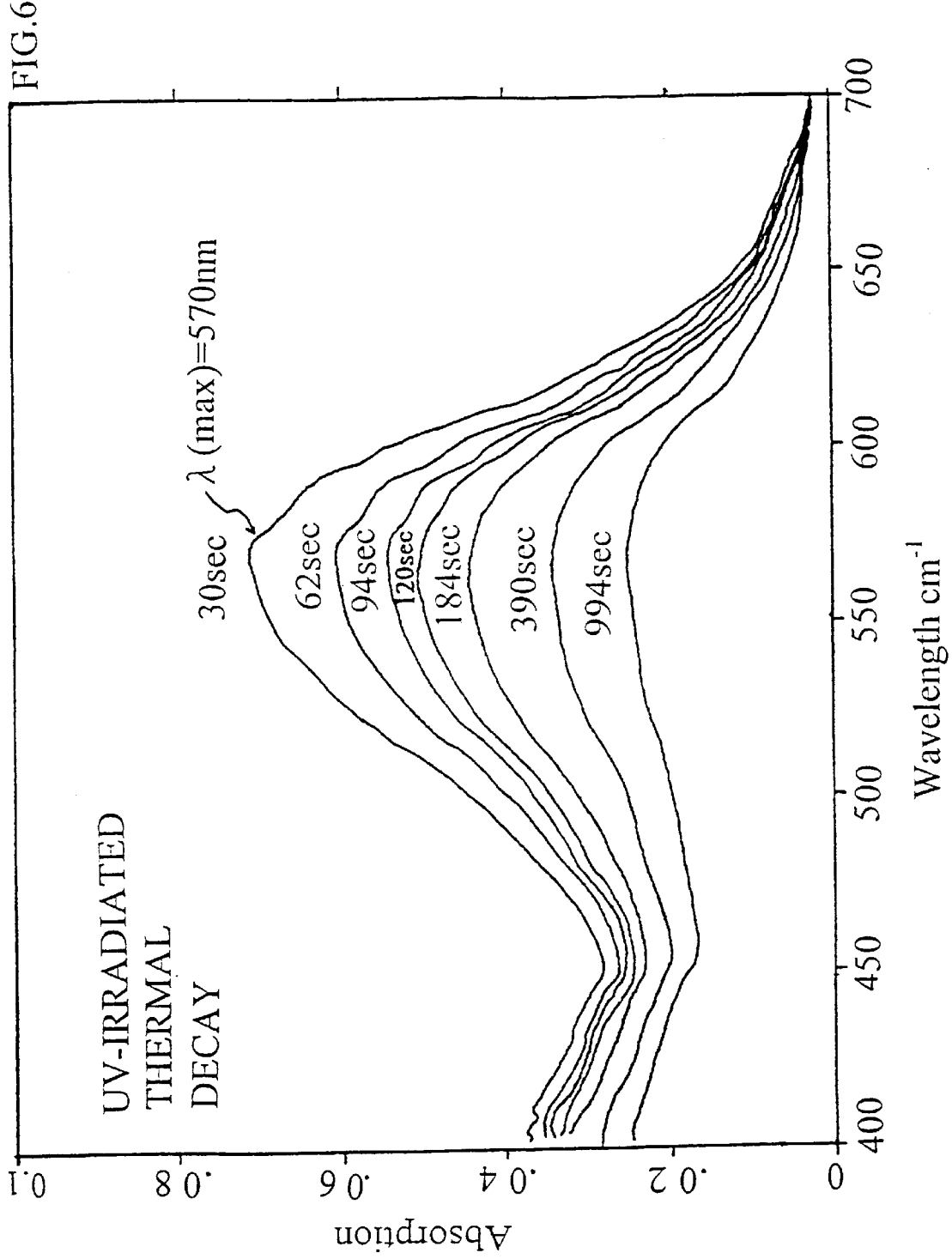
FIG. 6. UV absorption curves of copolymer (MMA/III) (containing 7 wt % of SO).
Figure 7:
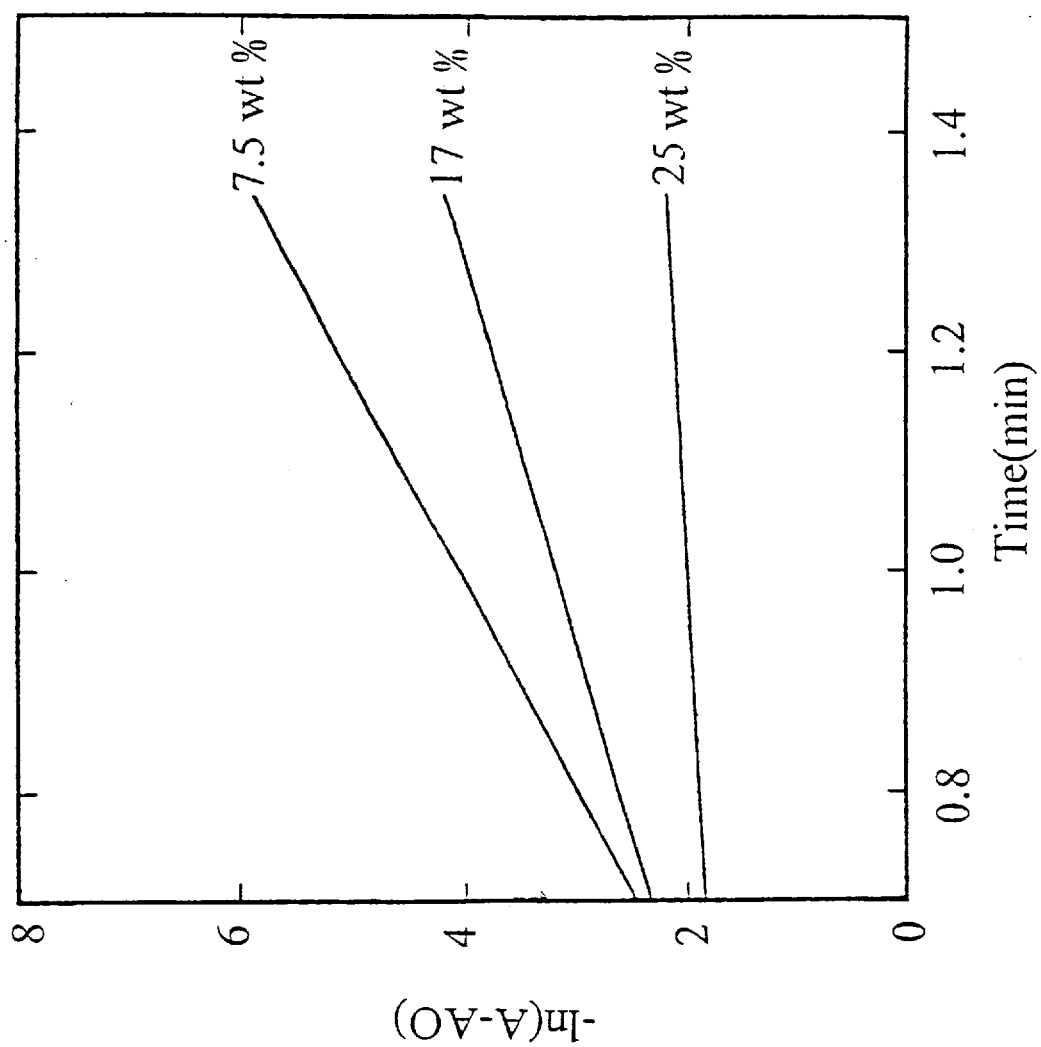
FIG. 7. Kinetics of the decoloration rate for films prepared by blending pigment(III) in PMMA(blending type).

Copolymers containing different amount of pigments (7.4%, 22%, 31%) obtained in example 5 were dissolved in tetrahydrofuran(THF) to make a 10 wt % high molecular weight solution. Operation steps in example 10 were filtered, coated, and dried. When a photochromic film was obtained eventually, the result of test showed that the maximum absorbance was 570 nm upon UV light exposure, as shown in FIG. 6.

Example 12

Kinetic properties of blending type of photochromic polymer film.

(a) Method of testing: the photochromic polymer film obtain in example 10 was exposed to a LISTED model 977 UV light (wavelength was set to be 365 nm, and power was 80 w) for 20 minutes, followed by measuring the absorbency using a Otsuka MCPD-1000 multiple frequencies detector (the light source was $I_2$). The detection was scanned every 16 ms. The change of absorbance versus time was recorded.

(b) data analysis

Data analysis was performed by using Kohlraush-Williams-Watts(KWW) equation:

$$-ln(A-A_0)=Kt^a+B$$

in a software developed by LOTUS, and decoloration constants at various concentrations were obtained as given in Table 8.

(c) Results of analysis for a blending-type polymer film

Based on our observations, the decoloration rate decreased while the concentration of pigment increased. When concentration of pigment is low, the free volume in PMMA furnish enough space for the rotation and mobility of spirooxazine (pigment III) to be a functional photochromic pigment. However, when concentration of pigment increased, isomerization was hindered, and the decoloration rate decreased. Moreover, simulation of decoloration by Kohlraush-Williams-Williams-Watts (KWW) equation: -In $(A-A_0)=Kt^a+B$, revealed that the photochromic behavior of pigment in PMMA was not a first order reaction.

Comparative Example 6

Kinetic study of bonding type of photochromic polymer film

Figure 8:
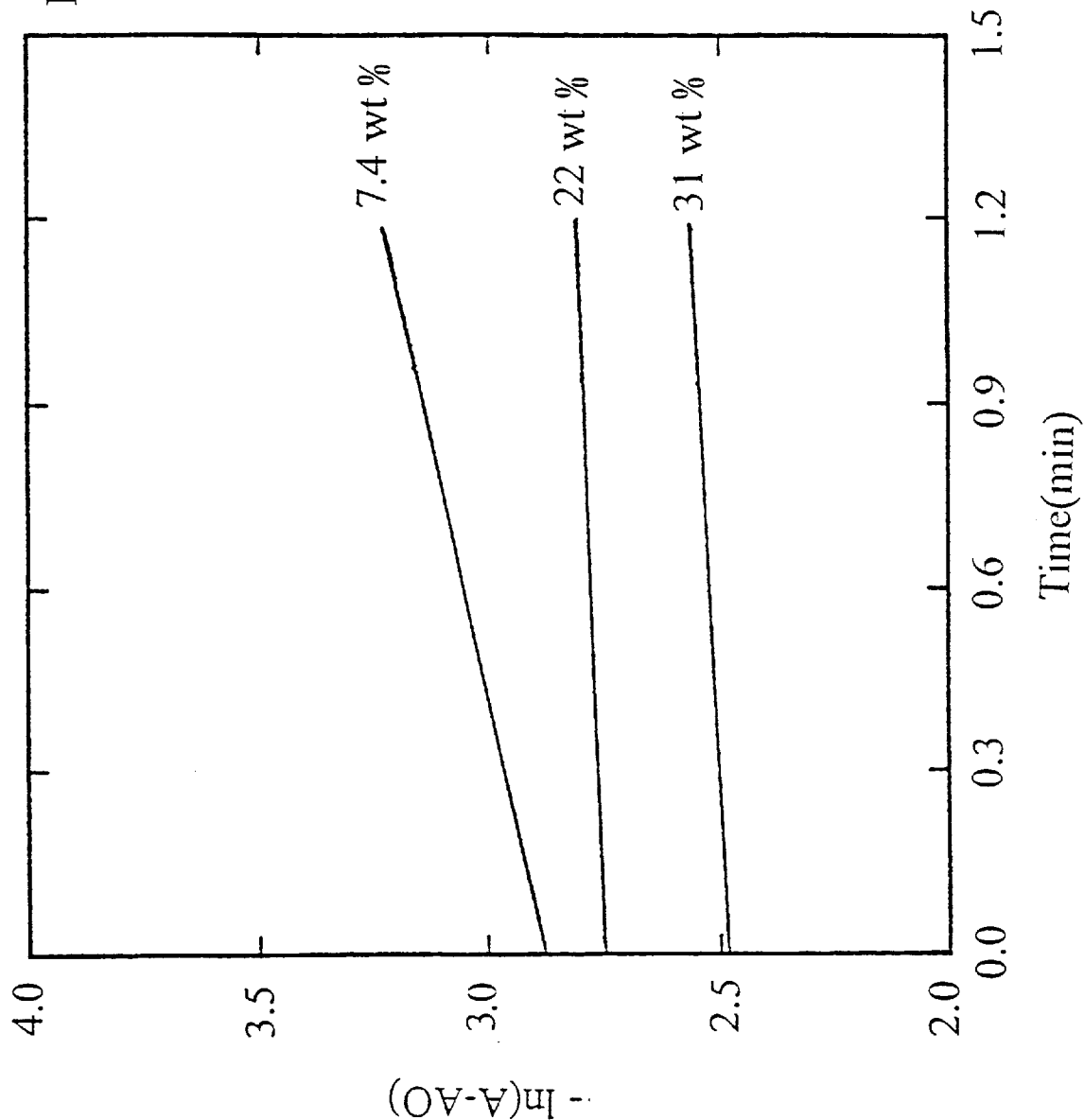
FIG. 8. Kinetics of the decoloration rate for films prepared by copolymerization of pigment (III) with MMA (bonding type).

The method for study was as same as in Example 12, except the photochromic polymer film was obtained from Example 11. After analyzed by MCPD-100 and KWW equation, results were obtained and shown in Table 9 and FIG. 8.

Comparative Example 7

Comparison of decoloration behavior between blending and bonding type of photochromic polymer films.

From rate constants obtained in Table 8 and Table 9, at the lower concentration (7.5 wt %), the rate constant of a blending-type photochromic polymer film is significantly greater than that of a bonding-type, this means the decoloration rate for blending-type a photochromic polymer film was faster. This is because the photochromic pigment is not bound in copolymers. Thus, upon UV light exposure, the mobility and rotation of photochromic pigment were higher, resulting in a higher rate constant. In copolymer, the rotation and mobility of photochromic pigment were hindered, a smaller rate constant was obtained. However, when the concentration of pigment increased, the decoloration rate in copolymer film was not lowered, while the rate constant became lower in the blending type. This is due to the result of phase separation and aggregation occurred between photochromic pigment and substrate unit. Based on these observations, it is concluded that chemical bonding is a better approach to prepare photochromic formulation because the following merits: (1) In the preparation of high concentration of photochromic pigments, problems such as phase separation and aggregation may be avoided. (2) When bonding method is chosen for the preparation of photochromic formulation, the concentration shows less influence on the decoloration rate. For this reason, this type of photochromic polymer can be applied to photoelectrical elements.

TABLE 1

Solution properties of pigment (III) and CSO

|  | pigment III | Commercial Spirooxazine (CSO) |
|---|---|---|
| chloroform | ○ | ○ |
| ethyl acetate | ○ | ○ |
| DMF | ○ | ○ |
| methanol | Δ | Δ |
| ether | ○ | ○ |
| acetone | ○ | ○ |
| benzene | ○ | ○ |
| toluene | ○ | ○ |
| n-hexane | X | X |

○: soluble
Δ: slightly soluble
X: insoluble

TABLE 2

Color change of photochromic pigments in organic solvent

| test item | maximum wavelength after light exposure ($\lambda$max) | color change | |
|---|---|---|---|
| type of pigment | | before light exposure | after light exposure |
| pigment (III) | 471 nm | colorless | yellow |
| CSO | 472 nm | colorless | yellow |

TABLE 3

Reaction conditions for synthesis of copoly (III)

| item | input of monomers (wt %) | | initiator concentration (AIBN) | reaction time | |
|---|---|---|---|---|---|
| polymer | MMA | III | wt % | (hrs) | solvent |
| PMMA | 100 | 0 | 0.25 | 10 | toluene |
| copolymer 10 | 90 | 10 | 0.25 | 10 | toluene |

TABLE 3-continued

Reaction conditions for synthesis of copoly (III)

| item | input of monomers (wt %) | | initiator concentration (AIBN) | reaction time | |
|---|---|---|---|---|---|
| polymer | MMA | III | wt % | (hrs) | solvent |
| copolymer 25 | 80 | 25 | 0.25 | 10 | toluene |
| copolymer 35 | 70 | 35 | 0.25 | 10 | toluene |

Note:
reaction temperature 80 °C.

TABLE 4

Analysis of pigment content in copolymers (MMA/III)

| | sample weight | N % | C % | H % | pigment (III) content |
|---|---|---|---|---|---|
| copolymer 10 | 2.337 mg | 0.38 | 60.62 | 7.76 | 7.61% |
| | 2.357 mg | 0.37 | 60.71 | 7.75 | 7.411% |
| copolymer 25 | 2.505 mg | 1.10 | 62.34 | 7.68 | 22.02% |
| | 2.560 mg | 1.13 | 62.46 | 7.75 | 22.62% |
| copolymer 35 | 2.538 mg | 1.56 | 64.09 | 7.61 | 31.32% |
| | 2.520 mg | 1.6429 | 64.10 | 7.51 | 32.81% |

TABLE 5

Properties of Copoly (MMA/III)

| item | molecular weight | | glass transition temperature |
|---|---|---|---|
| polymer | Mw | Mn | Tg (°C.) |
| copolymer 10 | 120,145 | 82,507 | 126.9 |
| copolymer 25 | 132,898 | 96,489 | 127.4 |
| copolymer 35 | 125,292 | 79,419 | 126.9 |

TABLE 6

Reaction conditions of synthesis of Copoly (AN/III)

| item | input ratio of monomer (wt %) | | concentration of initiator | reaction time | |
|---|---|---|---|---|---|
| polymer | AN | III | AIBN | (hrs) | solvent |
| PAN | 100 | 0 | 0.25 | 10 | DMF |
| copoly AN 10 | 90 | 10 | 0.25 | 10 | DMF |

Note: reaction temperature 70° C.

TABLE 7

Color change of photochromic fibers

| photochromic fiber | photochromic polypropylene fiber | | photochromic polyester fiber | |
|---|---|---|---|---|
| type of pigment | before UV exposure | after UV exposure | before UV exposure | after UV exposure |
| pigment (III) | light yellow | blue | light yellow | blue |

TABLE 8

Decoloration rate of photochromic polymer film prepared by pigment (III) with PMMA

| concentration of pigment (III) | rate of decoloration |
|---|---|
| 7.5 wt % | $-\ln(A - A_0) = 5.3481 t^{0.098} - 1.2860$ |
| 17 wt % | $-\ln(A - A_0) = 2.9166 t^{0.098} + 0.2767$ |
| 25 wt % | $-\ln(A - A_0) = 0.5202 t^{0.098} + 1.4860$ |

TABLE 9

Decoloration rate of photochromic polymer film prepared by copolymerization of pigment (III) with MMA monomer

| concentration of pigment (III) | rate of decoloration |
|---|---|
| 7.5 wt % | $-\ln(A - A_0) = 3.1037 t^{0.063} + 0.1197$ |
| 22 wt % | $-\ln(A - A_0) = 2.8505 t^{0.063} - 0.2886$ |
| 23 wt % | $-\ln(A - A_0) = 2.4745 t^{0.063} + 0.3329$ |

What is claimed is:

1. A reactive photochromic compound with excellent thermal and light resistance properties having the structure as shown below:

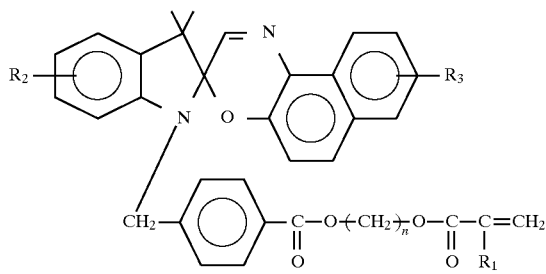

wherein $R_1$ is either a hydrogen atom or an alkyl group containing 1 to 5 carbon atoms, $R_2$ and $R_3$ are selected from the group consisting of hydrogen, halogen and an alkoxy group having 1 to 10 carbon atoms, wherein n represents the number of repeated units.

2. A process of making the compound as defined in claim 1 wherein said compound is 1-[4'-(2''-methacryloxy) ethoxycarbonyl][benzyl-3-3-dimethyl-spiro[indoline-2,3'-[3H]-naphtho[2,1-b]-1,4-oxazine] comprising reacting 4-chloromethylbenzoylchloride, 2-hydroxyethylmethacrylate, and pyridine to form 2-[4'-iodomethyl benzoyloxy]ethylmethacrylate, reacting said 2-[4'-iodomethyl benzoyloxy] ethylmethacrylate with 2,3,3-trimethyl indolenine to form 1-[4'-(2''-methacryloxy)ethoxycarbonyl]benzyl-3,3-dimethyl-2-methylene indolenine, reacting said 1-[4'-(2''-methacryloxy)ethoxycarbonyl] benzyl-3,3-dimethyl-2-methylene indolenine with 1-nitroso-2-naphthol to form 1-[4'-(2''-methacryloxy) ethoxycarbonyl] [benzyl-3-3-dimethyl-spiro[indoline-2,3'-[3H]-naphtho[2,1-b]-1,4-oxazine].

3. A method of making a photochromic composition comprising blending the photochromic compound as defined in claim 1 with at least one polymer.

4. A method of making a photochromic copolymer comprising polymerizing the photochromic compound as defined in claim 1 with at least one different monomer.

5. A method of making a photochromic composition comprising blending the photochromic compound as defined in claim 1 with at least one polymer and a copolymer comprising said photochromic compound.

6. The method of making a photochromic composition as defined in claim 3 wherein said polymer is at least one polymer selected from the group consisting of polyester, polydimethyl isophthalate, polypropylene, polymethyl methacrylate and polyethylene terephthlate.

7. The method of making a photochromic copolymer as defined in claim 4 wherein said monomer is at least one monomer selected from the group consisting of methyl methacrylate and acrylonitrile.

8. A method of making a photochromic fiber comprising forming a photochromic fiber from a blend of the photochromic compound as defined in claim 1 with at least one polymer.

9. A method of making a photochromic film comprising forming a photochromic film from a photochromic composition comprising the photochromic compound as defined in claim 1.

10. A method of making a photochromic film comprising forming a photochromic film from a photochromic copolymer comprising the photochromic compound as defined in claim 1.

11. A photochromic composition made by the process defined in claim 3.

12. A photochromic copolymer made by the process defined in claim 4.

13. A photochromic composition made by the process defined in claim 5.

14. A photochromic composition comprising the photochromic compound as defined in claim 1.

15. The photochromic composition as defined in claim 14 wherein said photochromic compound comprises 1 to 40 wt % of said photochromic composition.

16. A photochromic copolymer comprising the photochromic compound as defined in claim 1.

17. The photochromic copolymer as defined in claim 16 wherein said photochromic compound comprises 1 to 40 wt % of said photochromic copolymer.

* * * * *